United States Patent [19]

Lecount

[11] Patent Number: 5,187,190

[45] Date of Patent: Feb. 16, 1993

[54] PHENOXYPROPANOLAMINE COMPOUNDS

[75] Inventor: David J. Lecount, Congleton, Great Britain

[73] Assignee: Imperial Chemical Industries PLC, London, England

[21] Appl. No.: 608,475

[22] Filed: Nov. 2, 1990

[30] Foreign Application Priority Data

Nov. 6, 1989 [GB] United Kingdom ............... 8925032

[51] Int. Cl.$^5$ .......................................... C07C 217/36
[52] U.S. Cl. .................................. 514/652; 564/349; 564/351
[58] Field of Search ................. 514/652, 679, 699; 564/349, 351

[56] References Cited

U.S. PATENT DOCUMENTS

| 3,723,524 | 3/1973 | Augstein et al. ............... 564/165 |
| 3,780,081 | 12/1973 | LeCount et al. ............... 564/349 |
| 3,873,600 | 3/1975 | Brandstrom et al. ............ 560/29 |
| 3,903,091 | 9/1975 | Yamamoto et al. ............. 546/146 |
| 4,088,764 | 5/1978 | Raabe et al. ................. 514/256 |
| 4,146,638 | 3/1979 | Renth et al. ................. 514/522 |
| 4,191,765 | 3/1980 | Fritsch et al. ............... 514/464 |
| 4,263,323 | 4/1981 | Carlsson et al. .............. 514/620 |
| 4,329,358 | 5/1982 | Ainsworth et al. ............. 514/567 |
| 4,338,333 | 7/1982 | Ainsworth et al. ............. 514/539 |
| 4,460,580 | 7/1984 | Ostermayer et al. ............ 514/357 |
| 4,478,849 | 10/1984 | Ainsworth et al. ............. 514/445 |
| 4,636,511 | 1/1987 | Ostermayer .................. 514/311 |
| 4,697,033 | 9/1987 | Henrick ...................... 558/233 |
| 4,772,631 | 9/1988 | Holloway et al. .............. 564/349 |
| 4,927,836 | 5/1990 | Holloway et al. .............. 514/620 |

FOREIGN PATENT DOCUMENTS 1159072 12/1983 Canada .
0007294 1/1980 European Pat. Off. .
0064487 11/1982 European Pat. Off. .
0164700 12/1985 European Pat. Off. .
0171760 2/1986 European Pat. Off. .
10210849 2/1987 European Pat. Off. .
10254532 1/1988 European Pat. Off. .
1957706 5/1970 Fed. Rep. of Germany .
0022898 1/1989 Japan .
84/8004 4/1985 South Africa .
632987 11/1982 Switzerland .
1245148 9/1971 United Kingdom .
1589838 5/1981 United Kingdom .
2101119 1/1983 United Kingdom .

OTHER PUBLICATIONS

Chem Abstracts: vol. 98, No. 106954c (1983).
Chem Abstracts: vol. 98, No. 137626b (1983).
Chem Abstracts: vol. 89, No. 129247c (1978).
Chemical Abstracts, vol. 104, No. 224720p (1986).
Chemical Abstracts, vol. 104, No. 224722r (1986).

Primary Examiner—Carolyn Elmore
Assistant Examiner—Scott C. Rand
Attorney, Agent, or Firm—Cushman, Darby & Cushman

[57] ABSTRACT

Compounds of the formula (I):

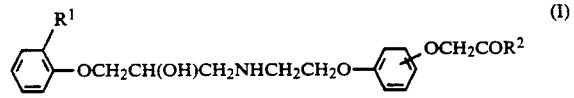

wherein $R^1$ is hydrogen or fluoro and $R^2$ is hydrogen or C1-6 alkyl and salts thereof are described as agents for the treatment of obesity and related conditions. Processes for their preparation and intermediates are described.

7 Claims, No Drawings

PHENOXYPROPANOLAMINE COMPOUNDS

The present invention relates to 2-hydroxy-3-phenoxypropylamino compounds and in particular to such compounds containing an alkanoylmethoxy group. This invention further relates to processes and intermediates for their preparation, to their use in methods of therapy and to pharmaceutical compositions containing them. Administration of the compounds of this invention to warm-blooded animals provides a thermogenic effect, that is thermogenesis is stimulated and administration of the compounds is of use, for example, in the treatment of obesity and related conditions such as obesity of mature onset diabetes.

Accordingly the present invention provides a compound of the formula (I):

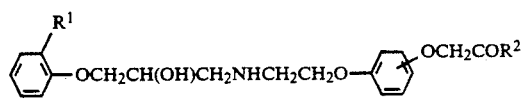 (I)

wherein $R^1$ is hydrogen or fluoro and $R^2$ is hydrogen or $C_{1-6}$alkyl, or a pharmaceutically acceptable salt thereof.

The —OCH$_2$COR$^2$ substituent in the compounds of the formula (I) is generally situated in the meta or para position of the phenyl ring relative to the phenoxypropylaminoethoxy substituent. Preferably the substituents are in a para relationship.

Preferably $R^1$ is hydrogen.

$R^2$ is hydrogen or $C_{1-6}$alkyl for example methyl, ethyl, n-propyl, isopropyl, n-butyl, isobutyl, n-pentyl and n-hexyl. Preferably $R^2$ is $C_{1-4}$alkyl for example methyl, ethyl or n-propyl. In particular $R^2$ is methyl or ethyl.

The compounds of the formula (I) are basic and may be isolated and used either in the form of the free base or of a pharmaceutically acceptable acid-addition salt thereof. Particular examples of pharmaceutically acceptable acid-addition salts include, for example, salts with inorganic acids such as hydrohalides (especially hydrochlorides or hydrobromides), sulphates and phosphates, and salts with organic acids such as succinates, citrates, lactates, tartrates, oxalates and salts derived from acidic water-soluble polymers.

It will be appreciated that the compounds of the formula (I) contain one or more asymmetric carbon atoms and can exist as optically active enantiomers or as optically inactive racemates. The present invention encompasses any enantiomer, racemate and/or (when two or more asymmetric carbon atoms are present) diastereoisomer, which when administered in a therapeutic amount provides a thermogenic effect in warm-blooded animals, it being well known in the chemical art how to prepare individual enantiomers, for example by resolution of the racemate or by stereospecific synthesis, and how to determine the thermogenic properties, for example, using the standard tests described hereinafter. It is preferred that the compounds of the present invention are provided in the (S) absolute configuration, at the —CH(OH)— group, (under the Cahn-Prelog-Ingold rules) which generally corresponds to the laevorotatory optically active form (—) in this class of compounds.

Particular compounds of the present invention include:

1-[4-(2-(2-hydroxy-3-phenoxypropylamino)ethoxy)-phenoxy]propan-2-one,
1-[4-(2-(2-hydroxy-3-phenoxypropylamino)ethoxy)-phenoxy]butan-2-one,
(S)-1-[4-(2-(2-hydroxy-3-phenoxypropylamino)ethoxy)-phenoxy]propan-2-one and
(S)-1-[4-(2-(2-hydroxy-3-phenoxypropylamino)ethoxy)-phenoxy]butan-2-one.

In order to use a compound of the present invention or a pharmaceutically acceptable salt thereof for the therapeutic treatment of warm-blooded mammals including humans, in particular for treating obesity, it is normally formulated in accordance with standard pharmaceutical practice as a pharmaceutical composition.

Therefore in another aspect the present invention provides a pharmaceutical composition which comprises a compound of the formula (I) or a pharmaceutically acceptable salt thereof and a pharmaceutically acceptable carrier.

The pharmaceutical compositions of this invention may be administered in standard manner for example by oral or parenteral administration. For these purposes they may be formulated by means known to the art into the form of, for example, tablets, capsules, pills, powders, aqueous or oily solutions or suspensions, emulsions, and sterile injectable aqueous or oily solutions or suspensions.

In general compositions for oral administration are preferred.

The compositions may be obtained using standard excipients and procedures well known in the art. A unit dose form such as a tablet or capsule will usually contain, for example 0.1–250 mg of active ingredient. The compositions may also contain other active ingredients known for use in the treatment of obesity and related conditions, for example appetite suppressants, vitamins and hypoglycaemic agents.

In one aspect of the present invention, a compound of the formula (I) may be formulated for oral administration in a sustained (or delayed) release composition, for example a matrix tablet formulation comprising insoluble or swellable polymeric filler, or a coated spheroid formulation.

When used to produce thermogenic effects in warm-blooded animals including man, a compound of the formula (I), or a pharmaceutically acceptable salt thereof as appropriate, will be administered so that a dose in the general range 0.002–20 mg/kg, and preferably in the range 0.02–10 mg/kg, is administered daily, given in a single dose or divided doses as necessary. However, it will be appreciated by those skilled in the art that dosage will necessarily be varied as appropriate, depending on the severity of the condition under treatment and on the age and sex of the patient and according to known medical principles.

In addition the compounds of the present invention lower triglyceride levels and cholesterol levels and raise high density lipoprotein levels and are therefore of use in combatting medical conditions wherein such lowering (and raising) is thought to be beneficial. Thus they may be used in the treatment of hypertriglyceridaemia, hypercholesterolaemia and conditions of low HDL (high density lipoprotein) levels in addition to the treatment of atherosclerotic disease such as of coronary, cerebrovascular and peripheral arteries, cardiovascular disease and related conditions.

Accordingly in another aspect the present invention provides a method of lowering triglyceride and/or cholesterol levels and/or increasing high density lipoprotein levels which comprises administering, to an animal in need thereof, a therapeutically effective amount of a compound of the formula (I) or pharmaceutically acceptable salt thereof. In a further aspect the present invention provides a method of treating atherosclerosis which comprises administering, to an animal in need thereof, a therapeutically effective amount of a compound of the formula (I) or pharmaceutically acceptable salt thereof. The compositions are formulated and administered in the same general manner as detailed above for producing a thermogenic effect. They may also contain other active ingredients known for use in the treatment of atherosclerosis and related conditions, for example fibrates such as clofibrate, bezafibrate and gemfibrozil; inhibitors of cholesterol biosynthesis such as HMG-CoA reductase inhibitors for example lovastatin, simvastatin and pravastatin; inhibitors of cholesterol absorption for example beta-sitosterol and (acyl CoA:-chlolesterol acyltransferase) inhibitors for example melinamide; anion exchange resins for example cholestyramine, colestipol or a dialkylaminoalkyl derivatives of a cross-linked dextran; nicotinyl alcohol, nicotinic acid or a salt thereof; vitamin E; and thyromimetics.

In a further aspect the present invention provides a process for preparing a compound of the formula (I) or a pharmaceutically acceptable salt thereof which process comprises:

a) reacting a compound of the formula (II) or (III) with a compound of the formula (IV):

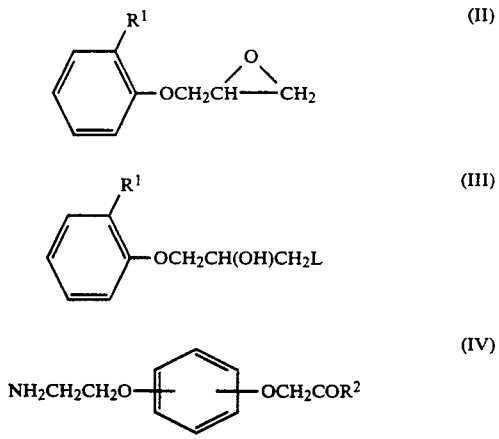

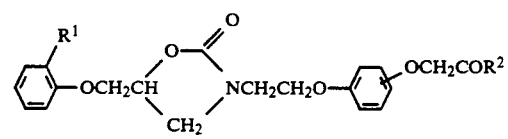

wherein $R^1$ and $R^2$ are as hereinbefore defined and L is a displaceable group; or b) hydrolysis of a compound of the formula (V):

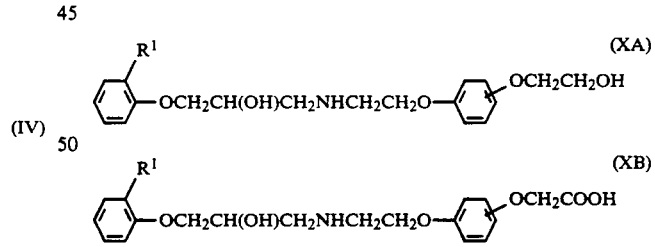

wherein $R^1$ and $R^2$ are as hereinbefore defined; or c) reacting a compound of the formula (VI) with a compound of the formula (VII):

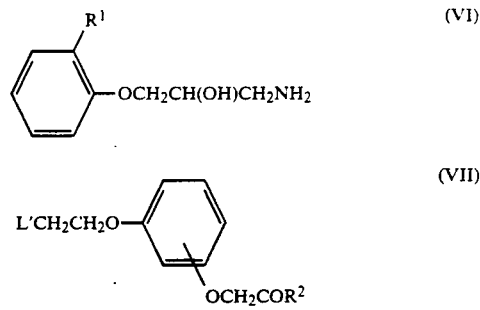

wherein $R^1$ and $R^2$ are as hereinbefore defined and L' is a leaving group; or d) reacting a compound of the formula (VIII) with a compound of the formula (IX):

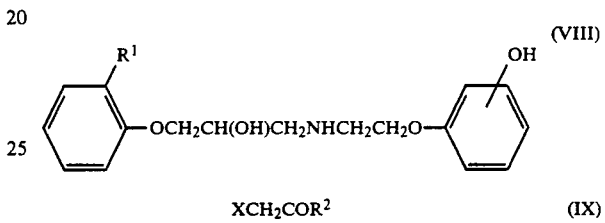

wherein $R^1$ and $R^2$ are as hereinbefore defined and X is a leaving group or a hydroxy group; or e) deprotecting a compound of the formula (X):

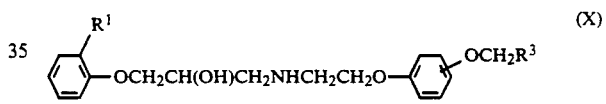

wherein $R^3$ is a protected derivative of the group —$COR^2$ and $R^1$ and $R^2$ are as hereinbefore defined; or f) for preparing a compound of the formula (I) wherein $R^2$ is hydrogen, oxidising a compound of the formula (XA) or reducing a compound of the formula (XB):

wherein $R^1$ is as hereinbefore defined;

and if necessary thereafter forming a pharmaceutically acceptable salt.

The reaction between a compound of the formulae (II) or (III) and a compound of the formula (IV) may be performed in a suitable solvent for example an alcohol such as ethanol or propan-2-ol, at a temperature in the range for example 10° C. to 110° C. and most conveniently at or near the boiling-point of the reaction mixture. In the compound of the formula (III) L may be for example halogen such as chloro or bromo or sulphonyloxy such as toluenesulphonyloxy or methanesulphonyloxy.

The compounds of the formula (IV) are prepared in any convenient manner known to those skilled in the art. For example they may be conveniently prepared by reacting compound (XI) with a compound of the formula (XII):

NH$_2$CH$_2$CH$_2$OH (XI)

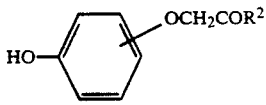 (XII)

For example this reaction may be performed using the Mitsunobu reaction with diethyl azodicarboxylate and triphenylphosphine. Desirably the amino function is protected during this reaction and subsequently deprotected in conventional manner. Examples of a suitable protecting group for the amino function include the phthaloyl and t-butoxycarbonyl groups.

The compound of the formula (V) may be hydrolysed to a compound of the formula (I) under conditions known in the beta-blocker art; for example via alkaline hydrolysis in a suitable solvent. The compounds of the formula (V) are novel and form another aspect of this invention.

The compounds of the formula (V) may be prepared by the reaction of a compound of the formula (XII) with a compound of the formula (XIII):

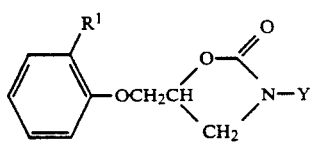 (XIII)

wherein R$^1$ is as hereinbefore defined and Y is —CH$_2$CH$_2$OH. This reaction may be performed in any conventional manner for example by a method analogous to the reaction of the compounds of the formulae (XI) and (XII). In an alternative the compounds of the formula (V) may be prepared by the reaction of a compound of the formula (XIII) wherein Y is hydrogen with a compound of the formula (VII) as hereinbefore described. In a further alternative the compounds of the formula (V) may be prepared by the reaction of a compound of the formula (II) with a compound of the formula (XIV):

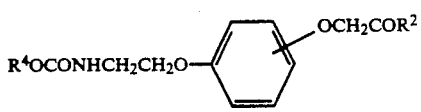 (XIV)

wherein R$^2$ is as hereinbefore defined and R$^4$O— is a leaving group, for example R$^4$O— is C$_{1-4}$alkoxy. In yet another alternative the compounds of the formula (V) may be prepared by reacting a compound of the formula (XIII) wherein Y is —CH$_2$CH$_2$Hal (for example Hal is bromine) with a compound of the formula (XII), typically in the presence of a base for example potassium carbonate.

The compound of the formula (XIII) wherein Y is —CH$_2$CH$_2$OH may be prepared for example by reaction of a compound of the formula (II) with an N-alkoxycarbonyl derivative of a compound of the formula (XI) for example t-butoxycarbonylaminoethanol which is preferably in protected form for example as the tetrahydropyranyl ether, with subsequent deprotection. The compounds of the formula (XIII) wherein Y is hydrogen or is —CH$_2$CH$_2$Hal are obtainable in conventional manner. The compounds of the formulae (VII) and (XIV) may be obtained by alkylation of the compounds of the formula (XII) in conventional manner.

The reaction between the compounds of the formulae (VI) and (VII) is conveniently performed under conditions analogous to the reaction between compounds of the formulae (III) and (IV). L' may have similar values as recited hereinabove for L.

In the compounds of the formula (IX) X is a leaving group, for example chloro, iodo, bromo, methanesulphonyloxy or p-toluenesulphonyloxy. The reaction of the compounds of the formulae (VIII) and (IX) is conveniently performed in the presence of an external base, for example an inorganic base such as an alkali metal carbonate or acetate (for example potassium carbonate or sodium acetate), or an alkali metal hydride (e.g. sodium hydride), and at a temperature in the range, for example, 10° to 120° C. A suitable solvent or diluent, for example acetone, methyl ethyl ketone, propan-2-ol, 1,2-dimethoxyethane or t-butyl methyl ether may conveniently be used. In order to minimise side-reactions, the process may also be carried out by pre-reacting the phenol of the formula (VIII) with a suitable base for example sodium hydride or potassium tert-butoxide, to form the corresponding salt which is then added to the alkylating agent of the formula XCH$_2$COR$^2$. In an alternative, in the compounds of the formula (IX), X is a hydroxy group. Such compounds may be reacted with compounds of the formula (VIII) using the conditions of the Mitsunobu reaction. Optionally the propanolamine moiety may be protected during such a Mitsunobu reaction, for example via an aminohemiacetal, such protection being readily removed thereafter.

The compounds of the formula (VIII) may be obtained by conventional procedures of organic chemistry. Thus, for example, they may be obtained by reaction of a phenol of the formula (XV):

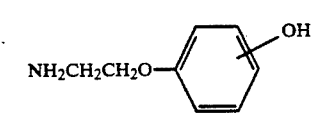 (XV)

with an epoxide of the formula (II) in a suitable solvent, for example, an alcohol such as ethanol or propan-2-ol, at a temperature in the range, for example, 10° to 110° C. and conveniently at or near the boiling point of the reaction mixture. The epoxides of the formula (II) are known per se but can be made by reaction of phenol or o-fluorophenol with epichlorohydrin or epibromohydrin in the presence of a suitable base such as an alkali metal hydroxide, piperidine, morpholine or N-methylmorpholine, in a suitable solvent or diluent such as methanol, ethanol or propan-2-ol, conveniently at or near the boiling point of the reaction mixture. In general, it is preferred to react the epoxide of the formula (II) with a protected phenol derivative of the formula (XVI):

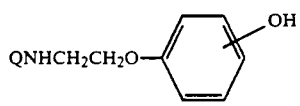

(XVI)

wherein Q is a suitable protecting group, such as benzyl. In this case, following the reaction of the compounds of the formulae (II) and (XVI), the protecting group is removed, for example in the case of benzyl by hydrogenolysis, for example using hydrogenation at a pressure in the range, for example, 1 to 30 bar in the presence of a palladium-on-carbon catalyst in an inert diluent or solvent for example, a $C_{1-4}$alkanol (such as methanol, ethanol or t-butyl alcohol) or a $C_{1-4}$alkanoic acid (such as acetic acid) and at a temperature of for example 20°–80° C.

The compounds of the formula (X) may be prepared by methods analogous to those described herein for the preparation of the compounds of the formula (I). $R^3$ is a protected derivative of the group -$COR^2$, for example $R^3$ may be an acetal such as dimethoxymethyl, diethoxymethyl, 1,3-dioxolan-2-yl, 2-methyl-1,3-dioxolan-2-yl or 2-ethyl-1,3-dioxolan-2-yl. Such groups may be readily converted to a group -$COR^2$ by acid hydrolysis for example with concentrated mineral acid at an elevated temperature. The compounds of the formula (X) are novel and form another aspect of this invention.

The compounds of the formulae (XA) and (XB) are known from, and prepared by the methods of, EP-A-210849. They may be oxidised or reduced, respectively, in conventional manner. For example suitable oxidising agents include ruthenium dichloride di(triphenyl)phosphine, quinolinium chlorochromate and ZrO(OCOCH$_3$)$_2$ in the presence of peracid. Suitable reducing agents include, for example, thexylborane or lithium/methylamine followed by treatment with aqueous ammonium chloride. In an alternative an ester of a compound of the formula (XB) may be reacted with diisobutylaluminium hydride to form the aldehyde.

Pharmaceutically acceptable salts may be prepared by reacting the compound of the formula (I) with the appropriate acid in conventional manner. Alternatively when a hydrogen halide salt is required, it may conveniently be obtained by hydrogenation of the free base together with a stoichiometric amount of the corresponding benzyl halide.

The following biological test methods, data and Examples serve to illustrate this invention.

The thermogenic effects of the compounds of the formula (I) may be demonstrated using one or more of the following standard tests:

(a) Rats are cold adapted at 4° C. for 4 days to increase their capacity for thermogenesis. They are then transferred to a warm environment of 23° C. for 2 days. On the following day, a test compound is administered sub-cutaneously or orally. Animals are sacrificed one hour later and the interscapular, brown adipose tissue (BAT) pad is removed. BAT mitochondria are prepared by differential centrifugation and GDP binding is determined (Holloway et al., *International Journal of Obesity*, 1984, 8, 295) as a measure of thermogenic activation. Each test includes a control which is dosed with the solution/suspension vehicle only and a positive control which is dosed with isoprenaline (as its sulphate) at 1 mgkg$^{-1}$. Test compounds are routinely dosed at 0.1, 0.3, 1.0, 3.0, and 10 mgkg$^{-1}$ and results expressed in terms of the effect on GDP binding produced by isoprenaline. From these results, a dose (ED$_{50}$) necessary to produce 50% of the isoprenaline effect is calculated by linear regression analysis. Compounds are considered active in this test if they cause a significant elevation in GDP binding as compared to controls.

(b) Rats are adapted to a thermoneutral environment (29° C.) for 2 weeks in order to decrease their capacity for BAT mediated non-shivering thermogenesis. During the final 3 days the animals are trained to use an apparatus for measuring heart rate non-invasively via foot-pad electrodes connected to an ECG integrator giving a continuous read-out of heart rate. A test compound is administered sub-cutaneously or orally at the ED$_{50}$ determined in test (a), and heart rate is determined 15–30 minutes after dosing. The procedure is then repeated in subsequent tests using increasing multiples of the ED$_{50}$ determined in test (a) until the heart rate (HR) reaches or exceeds 500 beats per minute, allowing the dose necessary to produce a heart rate of 500 beats per minute (D$_{500}$ dose) to be calculated.

The ratio of D$_{500}$ to ED$_{50}$ in test (a) can be defined as the selectivity index (SI) and provides a measure of the selectivity of the compound for BAT as opposed to the cardiovascular system. Compounds are considered to have significant selectivity which have an SI of $>1$. Non-selective compounds have an SI of $<1$ (for example isoprenaline=0.06).

(c) Rats are cold adapted at 4° C. for four days to increase their capacity for thermogenesis. They are then transferred to a warm environment at 23° C. for two days. On the following day, the basal metabolic rate of the animals is determined using a close-circuit oxygen consumption apparatus of the type described by Arundel et al., 1984, *J. Appl. Physiol. Respirat. Environ. Exercise Physiol.*, 1984, 57 (5) 1591–1593. The rats are then dosed (orally or sub-cutaneously) with test compound at about 1 mgkg$^{-1}$ as a solution or suspension in 0.45% w/v aqueous sodium chloride, 0.25% w/v Polysorbate 80. Metabolic rate is then determined for at least one hour after dosing. Compounds are considered active in this test if they cause a significant increase in metabolic rate as compared to control animals (Student's t test: $p<0.5$) dosed only the solution or suspension vehicle.

In the above tests, the compounds of the formula (I) in general produce effects of the following order without producing overt toxicity:

test (a): sub-cutaneous or oral ED$_{50}$ for GDP binding in BAT mitochondria of 0.01–10 mgkg$^{-1}$;

test (b): show an SI of $>50$; and test (c): show 2 ml O$_2$ min $^{-1}$Kg $^{0.75}$ at 1 mgkg$^{-1}$ p.o.

By way of illustration, the compound described in the accompanying Example 1, produced the following effects in the above tests:

(a) sub-cutaneous (oral) ED$_{50}$ 0.55 mgkg$^{-1}$;

(b) SI$>100$ (oral);

(c) 6.25 ml O$_2$ min $^{-1}$Kg $^{0.75}$ at 1 mgkg$^{-1}$ p.o.

The invention will now be illustrated by the following Examples in which, unless otherwise stated:

a) nuclear magnetic resonance (NMR) spectra were determined at 200 MHz in d$_6$-dimethylsulphoxide/d$_4$-acetic acid as solvent unless otherwise stated, using tetramethylsilane (TMS) as an internal standard and are expressed in delta values (parts per million) for protons relative to TMS, using conventional abbreviations to describe signal types.

b) chromatography was performed on Kieselgel (Art 9385; 230–400 Mesh) obtainable from E. Merck, Darmstadt, Federal Republic of Germany.

c) evaporations were carried out under reduced pressure using a rotary evaporator.

d) melting-points are uncorrected.

EXAMPLE 1

1-[4-(2-(2-Hydroxy-3-phenoxypropylamino)ethoxy)-phenoxy]propan-2-one.

1-[2-(4-(2-Methyl-1,3-dioxolan-2-ylmethoxy)phenoxy)-ethylamino]-3-phenoxypropan-2-ol (0.5 g) in a mixture of methanol (10 ml) and concentrated hydrochloric acid (10 ml) was stirred at 65° C. for 1 ½ hours. The reaction mixture was cooled, poured into water (30 ml), basified with sodium hydroxide solution and extracted into ethyl acetate (3×20 ml). The ethyl acetate extracts were washed with brine (2×20 ml), dried and the solvent removed under reduced pressure. The residual solid was converted to the hydrochloride and the salt crystallised from ethanol to yield white crystals of the title compound in the form of the hydrochloride (0.27 g); m.p. 166°–168° C.; microanalysis: found C, 60.7; H 6.3; N, 3.5%; required for $C_{20}H_{26}ClNO_5$, C, 60.7; H, 6.6; N, 3.5%; NMR 2.17(s,3H, COCH$_3$), 3.29–3.59 (m, 4H, CH$_2$NHCH$_2$), 4.06–4.08(m,2H, PhOCH$_2$CHOH), 4.30(t,2H, CH$_2$CH$_2$OAr), 4.40–4.44(m,1H, CHOH) 4.65(s,2H, OCH$_2$CO), 6.82–7.32(m,9H, aromatic H).

The starting material was prepared as follows:

a) Methyllithium (140 ml of 1.5 molar lithium bromide complex in diethyl ether) was added to a stirred solution of 4-hydroxyphenoxyacetic acid (7.6 g) in anhydrous tetrahydrofuran (500 ml) at 0°–10° C. under argon. The reaction mixture was stirred for 40 hours at 22° C., cooled in an ice-bath and chlorotrimethylsilane (39 ml) was added over 15 minutes. The temperature was allowed to rise to 22° C. and the reaction mixture was poured into 1N hydrochloric acid (360 ml) and stirred for 30 minutes. The product was extracted into ethyl acetate (4×200 ml) and the combined extracts washed with aqueous sodium bicarbonate (2×300 ml), brine (100 ml), dried and the solvent removed under reduced pressure. The crude ketone was purified by chromatography using 3½% tetrahydrofuran in dichloromethane as eluent. The appropriate fractions were combined and evaporated to yield 1-(4-hydroxyphenoxy)propan-2-one (2.0 g) as a white solid, m.p. 110°–112° C. (from ethyl acetate); microanalysis: found C, 65.5; H, 6.1%; required for $C_9H_{10}O_3$: C, 65.1; H, 6.0%. (A similar procedure for the preparation of methyl ketones is described by G. M. Rubottom and Chong-Wan Kim, J.O.C. 1983, 48, 1550–1552).

b) A solution of 1-(4-hydroxyphenoxy)propan-2-one (3.2 g), 1,2-ethanediol (3.0 ml) and p-toluenesulphonic acid (50 mg) in toluene (100 ml) was stirred under reflux in a Dean and Stark apparatus for 3 ½ hours in an atmosphere of argon. The reaction mixture was cooled, washed with 5% aqueous sodium bicarbonate (100 ml), washed with water (2×50 ml), washed with brine (50 ml) and dried. Toluene was removed under reduced pressure to give 4-[(2-methyl-1,3-dioxolan-2-yl)methoxy]phenol as an oil (3.4 g).

c) Diethyl azodicarboxylate (3.8 ml) was added dropwise to a stirred solution of 4-[(2-methyl-1,3-dioxolan-2-yl)methoxy]phenol (3.4 g), N-t-butoxycarbonylaminoethanol (5.2 g) and triphenylphosphine (6.3 g) in anhydrous tetrahydrofuran (100 ml), at ice-bath temperature, under argon. The reaction mixture was left for 64 hours at 25° C. and then the solvent was removed under reduced pressure. The residue was dissolved in ether (100 ml) and the ethereal solution washed with 2N aqueous sodium hydroxide (2×50 ml), water (2×50 ml) and saturated brine (50 ml). The aqueous washings were in turn extracted with ether (50 ml). The ethereal solutions were combined, dried, and the ether removed under reduced pressure. The residue was purified by chromatography using 1½% tetrahydrofuran in dichloromethane as eluent. The appropriate fractions were combined and evaporated to yield 1-t-butoxycarbonylamino-2-[4-((2-methyl-1,3-dioxolan-2-yl)-methoxy)phenoxy]ethane as a light yellow solid (3.2 g) m.p. 80°–82° C. (from cyclohexane); microanalysis: found C, 61.3; H, 7.7; N, 3.8%; required for $C_{18}H_{27}NO_6$: C, 61.2; H, 7.6; N 4.0%.

d) The product from c) above (2.9 g) was added to a stirred suspension of sodium hydride (0.39 g of 50% dispersion in mineral oil) in dry dimethylformamide (70 ml) under argon. The reaction mixture was stirred at 55° C. for 1 ½ hours. The mixture was cooled to 0° C., phenylglycidyl ether (1.1 ml) was added and the reaction mixture stirred at 55° C. for 1 ½ hours. The reaction mixture was cooled, poured into water (400 ml) and the product extracted into ethyl acetate (150 ml, 100 ml, 100 ml). The combined ethyl acetate extracts were washed with water (200 ml), dried and the solvent removed under reduced pressure. The residue was purified by chromatography using 35% hexane in ethyl acetate as eluent. The appropriate fractions were combined and evaporated to yield 3-[2-(4-(2-methyl-1,3-dioxolan-2-ylmethoxy)phenoxy)ethyl]-5-(phenoxymethyl)oxazolidin-2-one (1.1 g) m.p. 77°–79° C. (from ethyl acetate); microanalysis: found C, 64.5; H, 6.3; N, 3.1%; required for $C_{23}H_{27}NO_7$: C 64.3; H, 6.3; N, 3.3%.

e) A solution of the product from d) above (0.9 g) in a mixture of 2N aqueous sodium hydroxide (3 ml) and ethanol (15 ml) was heated under reflux under argon for 2 ½ hours. The reaction mixture was cooled, poured into water (25 ml) and the product extracted into dichloromethane (3×15 ml). The combined extracts were washed with brine (20 ml), dried, and the solvent removed under reduced pressure. The residue was purified by chromatography using 4% methanol in dichloromethane as eluent. The appropriate fractions were combined and evaporated to yield 1-[2-(4-(2-methyl-1,3-dioxolan-2-ylmethoxy)phenoxy)ethylamino]-3-phenoxypropan-2-ol (0.55 g) m.p. 95°–97° C. (from ethanol); microanalysis: found C, 65.2; H, 7.3; N, 3.5%; required for $C_{22}H_{29}NO_6$: C, 65.5; H 7.2; N, 3.5%.

In an alternative the product of part d) above may also be prepared as follows:

a) A solution of N-t-butoxycarbonylaminoethanol (2.0 g), dihydropyran (1.7 ml) and pyridinium p-toluenesulphonate (310 mg) in anhydrous dichloromethane (90 ml) was stirred at room temperature for 2 ½ hours. Ether (150 ml) was added, the solution was washed with water (2×50 ml), dried, and the solvent removed under reduced pressure to give 2-(2-(2-(N-t-butoxycarbonylamino)ethoxy)tetrahydropyran (3.0 g) as a yellow oil.

b) The product from a) above (2.9 g) was added to a stirred suspension of sodium hydride (570 mg of a 50% dispersion in mineral oil, 0.012 mol) in dry dimethylformamide (100 ml) under argon. The reaction mixture was stirred at 55° C. for 1 ½ hours. The mixture was cooled to 0° C., phenylglycidyl ether (1.6 ml) was added and the reaction mixture then stirred at 20° C. for 2½ hours. The reaction mixture was poured into water (500 ml) and the product extracted into ethyl. acetate (350 ml, 100 ml, 100 ml). The combined ethyl acetate extracts were washed with water (200 ml), dried, and the solvent removed under reduced pressure. The residue was subjected to chromatography using 40% hexane in ethyl acetate as eluent. The appropriate fractions were combined to yield 5-phenoxymethyl-3-(2-(tetrahydropyran-2-yloxy)ethyl)oxazolidin-2-one (1.0 g) m.p. 78°–80° C. (cyclohexane); microanalysis: found C, 63.3; H, 7.2; N, 4.3%; required for $C_{17}H_{23}NO_5$ C, 63.6; H, 7.2; N, 4.4%.

c) A solution of the product of b) above (0.88 g) and pyridinium p-toluenesulphonate (70 mg) in a mixture of water (1.0 ml) and ethanol (24 ml) was stirred at 65° C. for 4 hours. Ethanol was removed under reduced pressure and the residue partitioned between water (30 ml) and ethyl acetate (30 ml). The organic layer was separated and the aqueous layer re-extracted with ethyl acetate. The ethyl acetate extracts were washed with water (20 ml), dried, and the solvent removed under reduced pressure. Trituration of the residue with ether followed by crystallisation from propan-2-ol yielded 5-phenoxymethyl-3-(2-hydroxyethyl)oxazolidin-2-one (0.52 g) m.p. 89°–91° C.; microanalysis: found C, 60.8; H, 6.3; N, 5.8%; required for $C_{12}H_{15}NO_4$: C, 60.8; H, 6.3; N, 5.9%.

d) Diethyl azodicarboxylate (1.6 ml) was added dropwise to an ice-bath cooled, stirred, solution of 4-[(2-methyl-1,3-dioxolan-2-yl)methoxy]phenol (2.1 g), 5-phenoxymethyl-3-(2-hydroxyethyl)-oxazolidin-2-one (2.4 g) and triphenylphosphine (2.6 g) in anhydrous tetrahydrofuran (50 ml) under argon. The reaction mixture was left for 64 hours at 22° C. and then the solvent removed under reduced pressure. The residue was dissolved in dichloromethane and the solution seeded with 1,2-dicarbethoxyhydrazine. The solution was allowed to stand for 2 hours, the solid was collected and the filtrate was subjected to chromatography using 45% hexane in ethyl acetate grading to 40% hexane in ethyl acetate as eluent. The appropriate fractions were combined, evaporated, and the residue triturated with cyclohexane to give the 3-[2-(4-(2-methyl-1,3-dioxolan-2-ylmethoxy)phenoxy)ethyl]-5-(phenoxymethyl)oxazolidin-2-one (2.7 g) m.p. 75°–77° C.

EXAMPLE 2

1-[4-(2-(2-Hydroxy-3-phenoxypropylamino)ethoxy)phenoxy]butan-2-one 4-(2-(2-Hydroxy-3-phenoxypropylamino)ethoxy)phenol (0.5 g) was added to a stirred suspension of sodium hydride (82 mg of 50% dispersion in mineral oil) in anhydrous dimethylformamide (15 ml) under argon. The mixture was stirred at 20° C. for 2 hours. 1-Bromo-2-butanone (0.26 g) was added and the mixture was allowed to stand at 20° C. for 18 hours. The reaction mixture was poured into water (100 ml) and extracted into ethyl acetate (3×70 ml). The combined ethyl acetate extracts were washed with aqueous 1N sodium hydroxide (2×50 ml), brine (50 ml), dried and the solvent removed under reduced pressure. The residue was purified by chromatography using 4% methanol in dichloromethane as eluent. The appropriate fractions were combined and evaporated. The residual solid was converted to the hydrochloride and the salt crystallised from ethanol to yield white crystals of the title compound in the form of the hydrochloride (0.28 g); m.p. 159°–161° C.; microanalysis: found C, 61.5; H, 6.8; N, 3.3%; required for $C_{21}H_{28}ClNO_5$: C, 61.5; H, 6.8; N, 3.4%; NMR 0.95(t, 3H, $CH_3$), 2.48 (q, 2H, $CH_2CH_3$); 3.03–3.43 (m, 4H, $CH_2NHCH_2$), 3.90–4.03(m, 2H, $PhOCH_2CHOH$), 4.16–4.30(m, 3H, $CH_2CH_2OAr$+$CHOH$), 4.67 (s, 2H, $OCH_2CO$), 6.78–7.30(m, 9H, aromatic H).

The preparation of 4-(2-(2-hydroxy-3-phenoxypropylamino)ethoxy)phenol is described in European Patent Application 210849.

EXAMPLES 3 and 4

In a manner similar to that of Example 2, the following compounds as the hydrochloride salts were prepared from 1-bromo-2-pentanone and 1-bromo-2-octanone respectively.

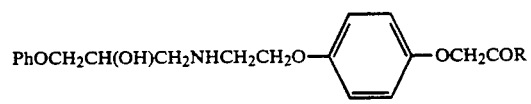

Example 3 (R=—$CH_2CH_2CH_3$) m.p. 162°–164° C. (ethanol); microanalysis: found C, 62.0; H, 7.4; N, 3.4%; required for $C_{22}H_{30}ClNO_5$: C, 62.3; H, 7.1; N, 3.3%; NMR 0.82(t, 3H, $CH_3$), 1.50(sextet, 2H, $CH_2CH_3$); 2.43(t, 2H, $COCH_2CH_2$); 3.05–3.40(m, 4H, $CH_2NHCH_2$); 3.89–4.02(m, 2H, $PhOCH_2CHOH$); 4.17–4.28(m, 3H, $CH_2CH_2OAr$+$CHOH$); 4.62(s, 2H, $OCH_2CO$); 6.76–7.26(m, 9H, aromatic H).

Example 4 (R=—$CH_2(CH_2)_4CH_3$) m.p. 163°–165° C. (ethanol;) microanalysis: found C, 64.2; H, 7.7; N, 2.9%; required for $C_{25}H_{36}ClNO_5$: C, 64.4; H, 7.7; N, 3.0%; NMR 0.86(t, 3H, $CH_3$); 1.20–1.36(m, 6H, $(CH_2)_3CH_3$); 1.43–1.60(m, 2H, $COCH_2CH_2$); 2.50(t, 2H, $COCH_2CH_2$); 3.08–3.46(m, 4H, $CH_2NHCH_2$); 3.93–4.09(m, 2H, $PhOCH_2CHOH$); 4.20–4.36(m, 3H, $CH_2CH_2OAr$+$CHOH$); 4.71(s, 2H, $OCH_2CO$); 6.82–7.36(m, 9H, aromatic H).

Scheme for the preparation of the compounds of examples 2–4 is set out below (wherein R is ethyl, n-propyl or n-hexyl)

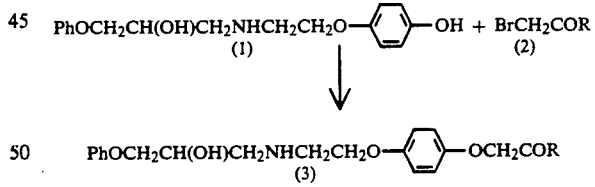

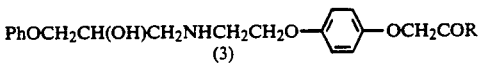

Footnotes:

A. 1-Bromo-2-pentanone (compound (2): R=—$CH_2CH_2CH_3$) was prepared as follows:

A solution of 1,2-epoxypentane was prepared by treating 1-pentene (4.9 g) in carbon tetrachloride (500 ml) with 3-chloroperoxybenzoic acid (24.2 g of 50–60%) for 16 hours at 20° C. with stirring. The reaction mixture was washed with aqueous sodium bisulphite, aqueous sodium carbonate and dried. A solution of bromine (11.2 g) in carbon tetrachloride (90 ml) was added over 30 minutes to a stirred and cooled (ice bath temperature) suspension of sodium carbonate (17.8 g) in the 1,2-epoxypentane solution while irradiating the reaction mixture with a 275 watt tungsten lamp. The reaction mixture was washed with water (300 ml), brine (200 ml), dried, and the solvent removed under reduced pressure. The residual oil was distilled to yield 1-bromo-2-pentanone (3.7 g); b.p. 66°-68° C. at 11 mbar. (A similar procedure for the preparation of bromoketones is described by V. Calo et al, Synthesis 1978, 139-140)

B. In a manner similar to that described in footnote A, 1-bromo-2-octanone was prepared from 1,2-epoxyoctane.

We claim:

1. A compound of the formula (I):

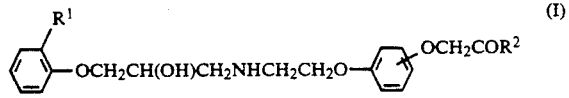

wherein $R^1$ is hydrogen or fluoro and $R^2$ is hydrogen or $C_{1-6}$ alkyl, or a pharmaceutically acceptable salt thereof.

2. A compound according to claim 1 wherein $R^1$ is hydrogen and the $—OCH_2COR^2$ substituent and the phenoxypropylaminoethoxy substituent are in para-relationship.

3. A compound according to claim 1 wherein $R^2$ is $C_{1-6}$ alkyl.

4. A compound according to claim 3 wherein $R^2$ is methyl or ethyl.

5. A compound according to claim 1 when in (S) absolute configuration at the $—CH(OH)—$ group.

6. A compound according to claim 1 which is:
1-[4-(2-(2-hydroxy-3-phenoxypropylamino)ethoxy)-phenoxy]propan-2-one,
1-[4-(2-(2-hydroxy-3-phenoxypropylamino)ethoxy)-phenoxy]butan-2-one,
(S)-1-[4-(2-(2-hydroxy-3-phenoxypropylamino)ethoxy)phenoxy]propan-2-one or
(S)-1-[4-(2-(2-hydroxy-3-phenoxypropylamino)ethoxy)phenoxy]butan-2-one.

7. A pharmaceutical composition which comprises a compound according to claim 1 or pharmaceutically acceptable salt thereof and a pharmaceutically acceptable carrier.

* * * * *